United States Patent [19]

Shinzawa

[11] Patent Number: 5,217,756
[45] Date of Patent: Jun. 8, 1993

[54] SELECTIVE CHEMICAL VAPOR DEPOSITION OF ALUMINUM, ALUMINUM CVD MATERIALS AND PROCESS FOR PREPARING THE SAME

[75] Inventor: Tsutomu Shinzawa, Tokyo, Japan
[73] Assignee: NEC Corporation, Tokyo, Japan
[21] Appl. No.: 875,657
[22] Filed: Apr. 29, 1992

Related U.S. Application Data

[62] Division of Ser. No. 712,772, Jun. 10, 1991, Pat. No. 5,130,459.

Foreign Application Priority Data

Jun. 8, 1990 [JP] Japan .................. 2-151042
Jun. 13, 1990 [JP] Japan .................. 2-152859

[51] Int. Cl.$^5$ ........................ C23C 16/00; H01L 21/28
[52] U.S. Cl. .......................... 427/252; 437/187
[58] Field of Search ............. 427/252, 576; 437/187

[56] References Cited

U.S. PATENT DOCUMENTS

| | | | |
|---|---|---|---|
| 3,445,493 | 5/1969 | Harwell | 556/187 |
| 3,453,093 | 7/1969 | Kobetz et al. | 556/187 |
| 4,328,261 | 5/1982 | Heinecke et al. | 427/252 |
| 5,091,210 | 2/1992 | Mikoshiba et al. | 427/576 |
| 5,130,459 | 7/1992 | Shinzawa | 556/178 |

FOREIGN PATENT DOCUMENTS 882214 11/1961 United Kingdom ............... 427/252

OTHER PUBLICATIONS

K. T. Tsubouchi et al., "Selective and Nonselective Deposition of Aluminum by LPCVD Using DMAH and Microregion Observation of Single-Crystal Aluminum with Scanning μ-RHEED Microscope" -*1990 Symposium on VSLI-Technology*-Jun. 4-7, 1990-pp. 5-6.

*Primary Examiner*—Paul E. Konopka
*Attorney, Agent, or Firm*—Sughrue, Mion, Zinn, Macpeak & Seas

[57] ABSTRACT

This invention provides a process for forming with high selectivity an Al film having good electrical conductivity at the uncoated portions of a substrate coated with a masking material by means of chemical vapor deposition, using an Al selective deposition material having good electrical conductivity without subjecting it preliminarily to cracking, characterized in that the process employs a molecular compound of trimethyl aluminum and dimethyl aluminum hydride as a starting material gas. This invention also provides an Al selective CVD material characterized in that it is an organic Al compound represented by the following formula:

$$(CH_3)_3Al-(CH_3)_2AlH$$

obtained through intermolecular binding between trimethyl aluminum and dimethyl aluminum hydride. This invention further provides a process for forming the Al selective CVD material, which comprises mixing a liquid trimethyl aluminum with a liquid dimethyl aluminum hydride in an inert gas atmosphere, followed by vacuum distillation of the mixture to give the desired compound represented by the above formula.

1 Claim, 2 Drawing Sheets

SELECTIVE CHEMICAL VAPOR DEPOSITION OF ALUMINUM, ALUMINUM CVD MATERIALS AND PROCESS FOR PREPARING THE SAME

This is a divisional of application No. 07/712,772 filed Jun. 10, 1991, now U.S. Pat. No. 5,130,459.

BACKGROUND OF THE INVENTION

This invention relates to a process for forming selectively an Al film or a silicon substrate by chemical vapor deposition, an Al selective deposition material to be used in the process and a process for preparing the same.

DESCRIPTION OF THE RELATED ART

Selective growth of Al film is applied, for example, in the formation of interconnection on a semiconductor substrate so as to achieve higher densification or planarization of the interconnection by filling the fine throughholes which has been impossible by the conventional sputtering process and to reduce the interconnection resistivity by application of an Al film to a polycrystalline silicon interconnection.

As the selective growth of Al film, a process using triisobutyl aluminum ((i-$CH_4H_9$)$_3$Al) has been reported as described in the Extended Abstracts of the 18th Conference on Solid State Devices and Materials (1986), pp. 755-756. In this process, selective formation of Al film is achieved by depositing Al selectively by means of chemical vapor deposition (CVD) onto the exposed portions of a silicon substrate having a silicon oxide pattern formed thereon.

However, the conventional process of the selective formation of Al films using triisobutyl aluminum suffers practical problems that the vapor pressure of the starting material triisobutyl aluminum is as low as 0.5 Torr at 25° C., and thus a sufficient amount of starting material cannot be fed, retarding the film formation speed by about two figures compared with that in the sputtering process currently employed in the processing of semiconductors, and that the starting material gas must preliminarily be subjected to vapor phase cracking.

No successful selective deposition of Al by thermal CVD using trimethyl aluminum has so far been reported. Although it was confirmed by the experiments made by the present inventor that the thermal CVD using dimethyl aluminum hydride can achieve such selective deposition, this process suffer problems that the selectivity is not necessarily exhibited to a sufficient level and further the resistivity of the thus formed Al film is greater than the one formed by the conventional process using triisobutyl aluminum (approximately the same as the ideal bulk resistivity).

SUMMARY OF THE INVENTION

This invention has been accomplished with a view to overcoming the problems inherent in the conventional processes and is directed to provide a process for selectively forming with high selectivity and Al film at a high deposition rate, an Al selective CVD material and a process for preparing the same.

One aspect of this invention to provide a process for selectively forming an Al film by means of chemical vapor deposition at the uncoated portions of a substrate coated with a masking material, characterized in that a molecular compound of trimethyl aluminum and dimethyl aluminum hydride is used as a starting material gas. Another aspect of this invention is to provide an Al selective CVD material characterized in that it is an organic Al compound represented by the following formula:

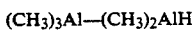

obtained through intermolecular binding between trimethyl aluminum and dimethyl aluminum hydride.

A further aspect of this invention is to provide a process for preparing the organic Al selective compound, which comprises mixing liquid trimethyl aluminum with liquid dimethyl aluminum hydride in an inert gas atmosphere, followed by vacuum distillation of the mixture to give the desired compound represented by the formula:

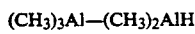

obtained through intermolecular binding between the trimethyl aluminum and the dimethyl aluminum hydride.

This invention will better be appreciated by reading the following detailed description of the invention referring to the attached drawings.

DESCRIPTION OF THE PREFERRED EMBODIMENTS

Figure 1:
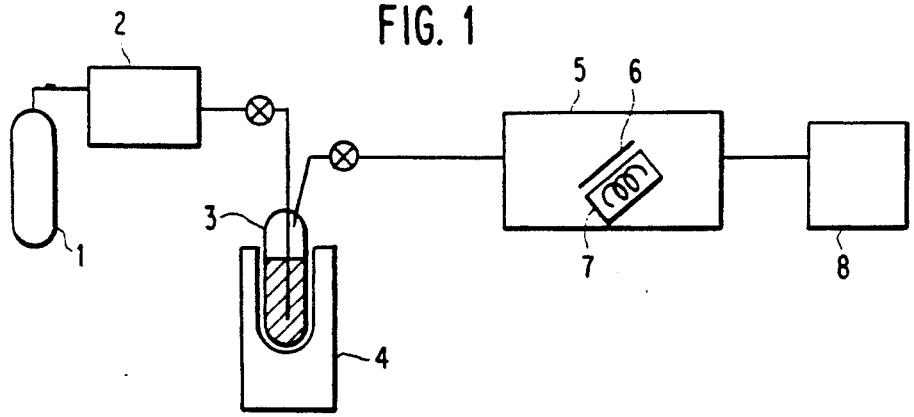
FIG. 1 shows a constitution of an exemplary apparatus to be used for selective formation of an Al film according to one embodiment of this invention.

In this invention the molecular compound of trimethyl aluminum (hereinafter abbreviated as TMA) and dimethyl aluminum hydride (hereinafter abbreviated as DMAH) is used as a starting material gas.

It was confirmed that the molecular compound of TMA and DMAH can form an Al film having excellent electrical conductivity with good selectivity and at a high film formation rate as the Al selective CVD material.

The vapor pressure of the starting material gas is relatively as high as the intermediate value of TMA's (12 Torr, 25° C.) and DMAH's (2 Torr, 25° C.). Accordingly, the feed of the raw material can be increased by the order of 1 to 2 figures compared with that of the conventional triisobutyl aluminum. It is known by experiments that at the temperature where the raw material shows selectivity, the film formation rate increases with the increase of feed, although the rate is not absolutely determined by the feed. Thus, the increase of feed can achieve increase of film formation rate by the order of one figure.

According to the new finding made by the present inventor after experiments, use of the molecular compound of TMA and DMAH is as a whole superior to the single use of DMAH in terms of selectivity and resistivity (approximately the same as bulk resistivity) of the Al film selectively deposited.

In the third aspect of this invention to prepare the molecular compound of TMA and DMAH, while a liquid TMA and a liquid DMAH are mixed, followed by distillation with heating, this action can be explained as follows.

TMA and DMAH are dimers which are stable at room temperature. As described in Journal of American Chemical Society, p. 3121 (1067), the TMA dimer has a bridge structure with the aluminum atoms being cross-linked via carbon atoms; whereas the DMAH dimer has a bridge structure with the aluminum atoms being cross-linked via hydrogen atoms as described in Chemical Communications p. 480 (1971). In the case of DMAH, since it has methyl groups in the molecule, the carbon atoms thereof can possibly be utilized in the crosslinking. However, the fact that hydrogen atoms are actually utilized in the crosslinking seems to prove better energy stability of the hydrogen atoms in achieving the crosslinking.

The crosslinking achieved via hydrogen atoms is more stable than in the crosslinking achieved via carbon atoms. Therefore, the TMA-DMAH molecular compound is more stable than the TMA dimer and a little less stable than the DMAH dimer, since the crosslinking in TMA-DMAH molecular compound is achieved via a hydrogen atom and a carbon atom.

When a mixture of TMA and DMAH is heated, the TMA dimer and DMAH dimer both undergo separation, and recombination of TMA and DMAH occurs to form a TMA-DMAH molecular compound; wherein by using the DMAH in a molecular weight of at least twice as much as the molecular weight of TMA, a mixture of DMAH dimer which is stabler than the TMA dimer and TMA-DMAH molecular compound which is stabler than the TMA dimer is resulted. At this temperature, since the vapor pressure of TMA-DMAH molecular compound is higher than that of DMAH, the TMA-DMAH molecular compound can be separated by vacuum distillation utilizing the difference in the vapor pressures. Now preferred embodiments of this invention will be described referring to the drawings.

Application of the present Al selective CVD material to selective CVD will first be described. FIG. 1 shows a constitutional view of a gas mixer and a vacuum CVD apparatus to be used for selective formation of an Al film; wherein 1 is a carrier gas tank, 2 a mass flow controller for controlling the flow rate of a carrier gas, 3 a bubbler vessel for mixing the starting material with the carrier gas, 4 a temperature adjuster for controlling the vapor pressure of the starting material in the bubbler, 5 a growth chamber, 6 a wafer, 7 a heater for adjusting the temperature of the wafer, and 8 an evacuation system.

The TMA-DMAH molecular compound is sealed in the bubbler vessel 3, and hydrogen gas is introduced thereto from the carrier gas tank 1 to mix it with the vapor of raw material in the bubbler vessel 3 under control of the hydrogen gas flow rate by the mass flow controller 2. The mixture is then introduced to the growth chamber 5 whose pressure is reduced to several Torr by the evacuation system 8.

In this process, the pressure in the growth chamber 5 is maintained to 1 Torr, and the carrier gas of hydrogen is controlled to 60 SCCM (cm$^3$/min as measured at 0° C. in terms of 1 atm) by the mass flow controller 2, with the temperature of the bubbler vessel 3 being maintained to 25° C. by the temperature adjuster 4; wherein the partial pressure of the raw material gas in the growth chamber is estimated to be 0.1 Torr. The wafer 6 placed in the growth chamber 5 is maintained by the heater 7 to the temperature where the starting material can show selectivity. The raw material introduced to the growth chamber 5 is heated on the wafer 6 to deposit Al thereon through pyrolysis.

Selective CVD was carried out using the TMA-DMAH molecular compound and DMAH, respectively, under the same conditions to compare film deposition rate, resistivity, surface condition and composition. The results are shown in Table 1.

TABLE 1

Comparison of TMA-DMAH molecular compound and DMAH in the film forming properties

| | Starting material | |
|---|---|---|
| Evaluation items | TMA-DMAH molecular compound | DMAH |
| Deposition rate ($\mu$m/min) | ca. 0.12 | ca. 0.22 |
| Resistivity ($\mu\Omega \cdot$cm) | 3.6 ± 0.1 | 7.0 ± 1.2 |
| Impurity content (atom %) | | |
| Si | 0.02 | 1.2 |
| C | 0.2 | 0.8 |
| O | 0.8 | 2.2 |
| H | 0.1 | 0.3 |
| Surface roughness (nm) | 25 | 75 |

As shown in Table 1 both TMA-DMAH molecular compound and DMAH showed relatively high deposition rates (about 0.12 $\mu$m/min vs about 0.22 $\mu$m/min). Resistivity of the TMA-DMAH molecular compound (ca. 3.6 $\mu\Omega$·cm) was higher than that of DMAH (ca. 7 $\mu\Omega$·cm), and the reason for the higher resistivity of DMAH seems to be attributable to the impurities contained in the film and roughness thereof. The impurity contents in the film was determined by SIMS analysis for the depth profiles of Si, C, O and H. As for the impurity contents in the Al films, DMAH showed higher Si concentration than in TMA-DMAH molecular compound by two figures, and several times higher concentrations of the other impurities. Selectivities of the two were compared by the number or density of the islands per unit area observable by an optical microscope (magnification 700). The island density when the TMA-DMAH molecular compound was used is by far smaller than when DMAH was used.

When CVD was carried out using the TMA-DMAH molecular compound on a silicon substrate having a silicon oxide pattern formed thereon, Al was deposited with good selectivity on the exposed portions of the silicon substrate through the opening of the masking pattern; wherein it was confirmed that sufficient selectivity can be exhibited in the temperature range of 220° to 250° C.

The effect of this invention can also be obtained by using other materials such as SiNx and PSG instead of the silicon oxide as used in the above embodiment. Further, while hydrogen was used as the carrier gas in the above embodiment, the effect of this invention can also be exhibited by use of argon or helium.

Incidentally, the means for feeding the TMA-DMAH molecular compound is not limited to the one exemplified in this embodiment, and as another effective means, for example, the two gas phase components can be transported from a bubbler having a TMA solution sealed therein and a bubbler having DMAH solution sealed therein using hydrogen as a carrier gas, respectively, to be mixed at a section immediately upstream the growth chamber 5.

Figure 2A:
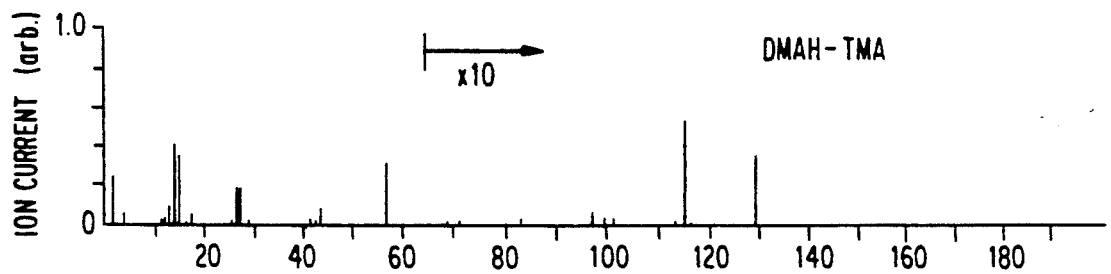
FIGS. 2a, 2b and 2c show mass spectra of the Al selective CVD material and of the starting materials thereof to be used according to this invention.

Next, the properties of the raw material gas used for Al selective CVD will be described. FIG. 2(a) shows a mass spectrum of the vapor phase component of the TMA-DMAH molecular compound which is the Al selective CVD material of this invention containing helium as a carrier gas determined by quadrupole mass spectrometer. For the purpose of comparison, FIGS. 2(b) and 2(c) show mass spectra of TMA and DMAH, respectively.

The axis of ordinates show ion current and the axis of absissas shows mass/unit electric charge (m/e). The same peaks of ion current were observed in all of these spectra at m/e=2, 15, 16, 27, 42, 43 and 57. The fragment observed at m/e=4 is of the helium carrier gas, while the fragments at m/e=17, 18 and 28 are of background impurities.

A fragment specific to the TMA-DMAH molecular compound (mass=130) is observed at m/e=115, which is of the $(CH_3)_4Al_2H^+$ separated from the TMA-DMAH molecular compound upon fragmentation.

Figure 2B:
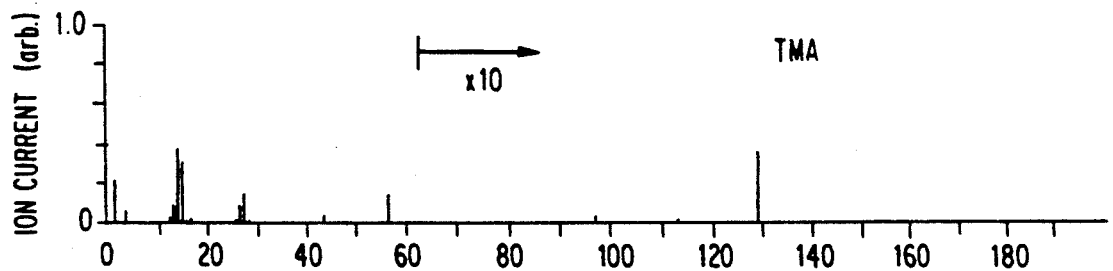
Figure 2C:
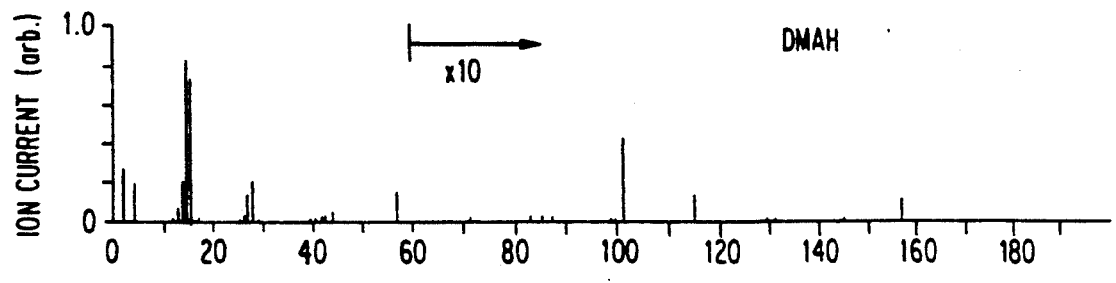

On the other hand, a fragment is observed at m/e=129 in the mass spectrum pattern of TMA shown in FIG. 2(b), which is of the $(CH_3)_5Al_2^+$ separated from the TMA dimer upon ionization. Fragments specific to DMAH are observed at m/e=101 and 115 in the mass spectrum pattern of DMAH, which are of the $(CH_3)_3Al_2H_2^+$ and of the $(CH_3)_4Al_2H^+$ separated from the DMAH dimer (mass=116), respectively.

The TMA-DMAH molecular compound can be determined by the presence of fragment at m/e=115 from the mass spectrum of the starting material gas.

Figure 3A:
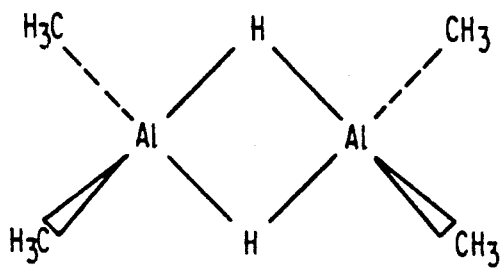
FIGS. 3a and 3b show the molecular structures of the Al selective CVD material and of the starting material thereof.
Figure 3B:
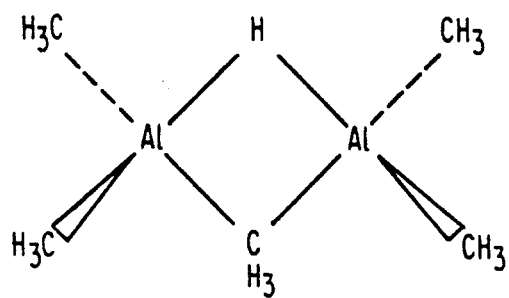

Now, the chemical structure of the TMA-DMAH molecular compound will be discussed. As described in Chemical Communications, p. 480 (1971), the DMAH dimer has been proved to have a bridge structure where the two Al atoms are crosslinked via hydrogen atoms by electron beam diffraction as shown in FIG. 3(a). Thus, it can be seen that the Al atoms can be crosslinked more stably by hydrogen atoms than by methyl groups.

Accordingly, it can be concluded that the TMA-DMAH molecular compound has a structure where the two Al atoms are linked via a methyl group and a hydrogen atom.

Figure 4:
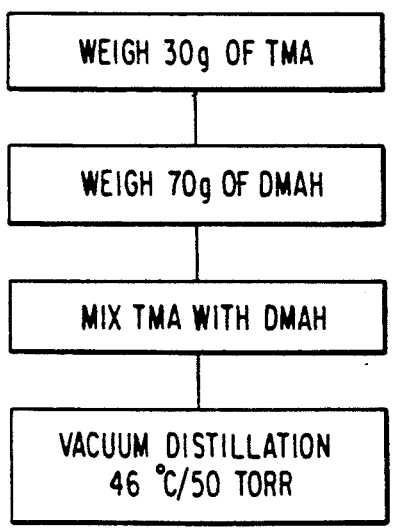
FIG. 4 is a flow chart showing an exemplary process for preparing the Al selective deposition material to be used according to this invention.

Next, the present process for preparing the Al selective CVD material will be described. FIG. 4 is a flow chart showing the process for preparing the Al selective CVD material to be used according to this invention. The entire process is carried out in an inert gas atmosphere or in an atmosphere where only the starting materials are present, since TMA, DMAH and the product to be formed therefrom are readily reactive with water and oxygen.

A liquid TMA and a liquid DMAH are weighed, respectively, at the weight ratio of the former to the latter of 3:7 at room temperature and they are mixed by stirring. The mixing can be carried out with heating to accelerate formation of the molecular compound, and vacuum distillation was used in this embodiment under the conditions of 46° C. temperature and 50 Torr pressure. The thus obtained TMA-DMAH molecular compound can form an Al film having good electrical conductivity by thermal CVD with excellent selectivity.

As described heretofore, this invention provides a process for forming an Al film by CVD using an Al selective deposition material which can form with high selectivity an Al film having good electrical conductivity without subjecting it preliminarily to cracking.

Further, according to the process of this invention the Al selective deposition material can easily be prepared from TMA and DMAH which have conventionally been used.

What is claimed is:

1. A process for selectively forming an aluminum film by means of chemical vapor deposition, comprising
    coating a substrate with a masking material such that uncoated portions remain on the substrate, and
    conducting chemical vapor deposition at the uncoated portions of the substrate by using a molecular compound of trimethyl aluminum and dimethyl aluminum hydride as a starting material gas to form the aluminum film.

* * * * *